(12) United States Patent
Lee et al.

(10) Patent No.: US 12,020,373 B2
(45) Date of Patent: Jun. 25, 2024

(54) METHOD FOR REPLAYING SCANNING PROCESS

(71) Applicant: MEDIT CORP., Seoul (KR)

(72) Inventors: Dong Hoon Lee, Goyang-si (KR); Won Hoon Choi, Seoul (KR)

(73) Assignee: MEDIT CORP., Seoul (KR)

( * ) Notice: Subject to any disclaimer, the term of this patent is extended or adjusted under 35 U.S.C. 154(b) by 137 days.

(21) Appl. No.: 17/401,250

(22) Filed: Aug. 12, 2021

(65) Prior Publication Data

US 2021/0375031 A1     Dec. 2, 2021

Related U.S. Application Data

(63) Continuation of application No. PCT/KR2020/002133, filed on Feb. 14, 2020.

(30) Foreign Application Priority Data

Feb. 15, 2019  (KR) .......................... 10-2019-0017680
Feb. 14, 2020  (KR) .......................... 10-2020-0018162

(51) Int. Cl.
*G06F 3/048*     (2013.01)
*A61C 9/00*     (2006.01)
(Continued)

(52) U.S. Cl.
CPC ............ *G06T 17/00* (2013.01); *A61C 9/0053* (2013.01); *G06F 3/0481* (2013.01);
(Continued)

(58) Field of Classification Search
CPC ........... G06T 17/00; G06T 7/70; G06T 19/20; A61C 9/0053; G06F 3/0481; G06F 3/04842

See application file for complete search history.

(56) References Cited

U.S. PATENT DOCUMENTS 9,707,054 B2 *   7/2017  Chishti .................. A61C 7/002
10,996,813 B2 *  5/2021  Makarenkova ..... G06F 3/04845
(Continued)

FOREIGN PATENT DOCUMENTS

JP     2012-529352 A     11/2012
JP     2018-175227 A     11/2018
(Continued)

OTHER PUBLICATIONS

International Search Report dated May 25, 2020 for PCT/KR2020/002133 and its English translation.
(Continued)

*Primary Examiner* — David Phantana-angkool
(74) *Attorney, Agent, or Firm* — Insight Law Group, PLLC

(57) ABSTRACT

In method for replaying a scanning process according to the present invention, position information and rotation information of a scanner are acquired while scanning a scan target is a scanning step, and the distance relationship and angle relationship with the scan target can be calculated according to the position information and rotation information of the scanner. The acquired information and relationship values can be linked with a scan time and stored, and scanning data, along with the acquired information, can be sequentially displayed over time in a display step. According to the method for replaying a scanning process, the process of scanning performed by a user can be examined in chronological order, and the examination process can be quickly performed by controlling replay speed and selecting scan time. Accordingly, there are advantages in that the user can perform additional scanning of inadequately scanned portions, and the results of the scan can be used as material for deriving an optimal path for scanning when performing a scan on another patient having a similar oral cavity shape.

20 Claims, 15 Drawing Sheets

(51) Int. Cl.
  *G06F 3/0481* (2022.01)
  *G06F 3/04842* (2022.01)
  *G06T 7/70* (2017.01)
  *G06T 17/00* (2006.01)
  *G06T 19/20* (2011.01)

(52) U.S. Cl.
  CPC ............ *G06F 3/04842* (2013.01); *G06T 7/70* (2017.01); *G06T 19/20* (2013.01); *G06F 2203/04804* (2013.01); *G06T 2200/08* (2013.01); *G06T 2200/24* (2013.01); *G06T 2207/30036* (2013.01); *G06T 2207/30244* (2013.01); *G06T 2210/41* (2013.01); *G06T 2219/2004* (2013.01)

(56) References Cited

U.S. PATENT DOCUMENTS

| | | | | |
|---|---|---|---|---|
| 11,622,836 | B2* | 4/2023 | Shojaei | G16H 30/20 345/419 |
| 2009/0098502 | A1* | 4/2009 | Andreiko | A61C 7/002 433/24 |
| 2010/0281370 | A1* | 11/2010 | Rohaly | G06T 15/205 715/810 |
| 2014/0120493 | A1* | 5/2014 | Levin | A61C 9/0066 433/29 |
| 2016/0175068 | A1* | 6/2016 | Cai | A61C 7/002 700/98 |
| 2016/0302895 | A1 | 10/2016 | Rohaly et al. | |
| 2017/0140511 | A1* | 5/2017 | Levin | G06T 5/006 |
| 2018/0096465 | A1* | 4/2018 | Levin | A61B 6/145 |
| 2018/0192964 | A1* | 7/2018 | Stalder | A61B 90/50 |
| 2019/0244332 | A1* | 8/2019 | Levin | A61C 9/0053 |
| 2019/0290408 | A1* | 9/2019 | Fisker | A61C 13/0004 |
| 2020/0202497 | A1* | 6/2020 | Levin | A61C 9/0053 |
| 2020/0214801 | A1* | 7/2020 | Wang | A61C 7/002 |
| 2021/0045843 | A1* | 2/2021 | Pokotilov | G16H 20/40 |
| 2021/0196429 | A1* | 7/2021 | Shojaei | A61C 7/002 |
| 2023/0004276 | A1* | 1/2023 | Makarenkova | A61C 7/002 |
| 2023/0068727 | A1* | 3/2023 | Saphier | G06T 7/70 |
| 2023/0071852 | A1* | 3/2023 | Roslyakova | A61C 13/0004 |
| 2023/0131313 | A1* | 4/2023 | Chekh | G06T 7/0012 433/215 |
| 2023/0132126 | A1* | 4/2023 | Chekh | G06V 40/171 433/24 |
| 2023/0414322 | A1* | 12/2023 | Chekh | A61C 7/002 |

FOREIGN PATENT DOCUMENTS

| | | |
|---|---|---|
| KR | 10-2015-0057800 A | 5/2015 |
| KR | 10-2015-0082428 A | 7/2015 |
| KR | 10-2016-0149301 A | 12/2016 |
| KR | 10-2018-0107324 A | 10/2018 |
| KR | 10-1915215 B1 | 11/2018 |
| WO | 2018-088610 A | 5/2018 |

OTHER PUBLICATIONS

The extended European Search Report dated Sep. 21, 2022 for European Application No. 20755610.1.
Korean office action dated Jan. 22, 2021 from Korean Intellectual Property Office for Korean Application No. 10-2020-0018162.
Chinese office action dated Feb. 11, 2023 for Chinese Application No. 202080014353.0.

* cited by examiner

METHOD FOR REPLAYING SCANNING PROCESS

CROSS-REFERENCE TO RELATED APPLICATIONS

This application is a continuation application of International Application No. PCT/KR2020/002133, filed Feb. 14, 2020, which claims the benefit of Korean Patent Application Nos. 10-2019-0017680, filed Feb. 15, 2019, and 10-2020-0018162, filed Feb. 14, 2020, in the Korean Intellectual Property Office, the disclosures of which are incorporated herein in their entirety by reference.

TECHNICAL FIELD

The present disclosure relates to a method of replaying a process of obtaining scan model data obtained through a scanner.

BACKGROUND ART

A three-dimensional (3-D) scanner a machine capable of obtaining and digitizing information on a shape of an object, that is, a scan target, and performs measurement on the object by projecting light onto the object. 3-D scan data is used in fields, such as the fabrication of vehicles, the fabrication of figures, quality tests, medical fields, and customerization, and the range of use thereof tends to be gradually expanded.

For example, in general, in a dental clinic, etc., an intraoral tissue structure, such as teeth, is checked through impression taking for teeth of a patient. Treatment and a cure are performed based on the checking of the intraoral tissue structure. In order to obtain 3-D information of the intraoral tissue structure, an oral scanner system for dental surgery which implements a 3-D modeling image of the intraoral tissue structure by using a measurement light, such as a laser, is recently widely used.

In the case of a common scanning device for a 3-D object, if a 3-D object is scanned, in order represent the complexity of the 3-D object, 3-D scan data is generated by generating a large amount of geometry information called polygons and performing an operation on the geometry information. When the scan task is terminated and the data is stored, the state in which the scanning has been completed may be checked, but there is a problem in that it is difficult to check the process of actually performing the scanning.

DISCLOSURE

Technical Problem

An object of the present disclosure is to provide a method of replaying a scanning process, which can simulate and display a scanning process of obtaining previously stored scan data from scan data.

Technical objects of the present disclosure are not limited to the aforementioned technical object, and other technical objects not described above may be evidently understood by those skilled in the art from the following description.

Technical Solution

A method of replaying a scanning process according to the present disclosure may include a scanning step of obtaining scan data by scanning a scan target by using a scanner, an information acquisition step of obtaining state information of the scanner obtained in the scanning step, a calculation step of calculating relative information between the scanner and the scan target based on the state information of the scanner obtained in the information acquisition step, and a display step of displaying, in a user interface, the scan data obtained by scanning the scan target.

Furthermore, the scanning step may include a two-dimensional (2-D) image acquisition step of obtaining at least one 2-D image data by receiving light incident through an opening part formed at one end of the scanner, a three-dimensional (3-D) image generation step of converting, into 3-D volume data, the at least one 2-D image data obtained in the 2-D image acquisition step, and an alignment step of aligning a plurality of the 3-D volume data so that the 3-D volume data is connected and aligned.

Furthermore, the information obtained in the information acquisition step may include position information and rotation information of a camera.

Furthermore, the position information of the camera may be obtained in the form of a 3-D orthogonal Cartesian coordinate system represented as x, y, and z values.

Furthermore, the rotation information of the camera may be obtained in the form of a 3×3 rotation matrix.

Furthermore, the position information of the camera and the rotation information of the camera may be obtained together in the form of a 3×4 matrix.

Furthermore, in the information acquisition step, position information and rotation information of a scanner tip may be obtained based on the position information of the camera and the rotation information of the camera.

Furthermore, the position information and rotation information of the scanner tip may be formed to operate in conjunction with a scan time.

Furthermore, in the display step, a process of forming the scan data may be replayed in a way to be sequentially displayed over time.

Furthermore, in the display step, in replaying the process of forming the scan data, a replay speed may be adjustable through a replay speed control unit formed in the user interface.

Furthermore, in the display step, in replaying the process of forming the scan data, a replay position may be adjustable through a scan time indication unit formed in the user interface.

Furthermore, in the display step, in replaying the process of forming the scan data, one end of a shape of the scanner including a scanner tip may be displayed in the user interface.

Furthermore, the shape of the scanner may be semi-transparently displayed in the user interface, and the state and scan data of the scanner including the scanner tip may be simultaneously replayed.

Furthermore, in the display step, a moving path of the scanner tip may be additionally displayed.

Furthermore, the moving path of the scanner tip may include scan time information. When a part in the moving path of the scanner tip is selected, the scanner tip may move to a replay position corresponding to the part.

Furthermore, the scan data and the position information and rotation information of the scanner tip may be divided into a plurality of groups in a time sequence.

Advantageous Effects

According to the method of replaying a scanning process according to an embodiment of the present disclosure, a process of performing a scan task can be simulated in a time sequence by implementing a scanning process of obtaining scan data in the form of a replay image.

Accordingly, information, including an environment in which a scan task performed to obtain scan data performed, a scanning method and a problem occurring during scanning, can be checked along a flow in which the scan task is performed. The checked information may be used to evaluate the reliability of the scan data, or reference may be made to the checked information as a guide for improving efficiency when a next scan task is performed.

DESCRIPTION OF REFERENCE NUMERALS

Figure 1:
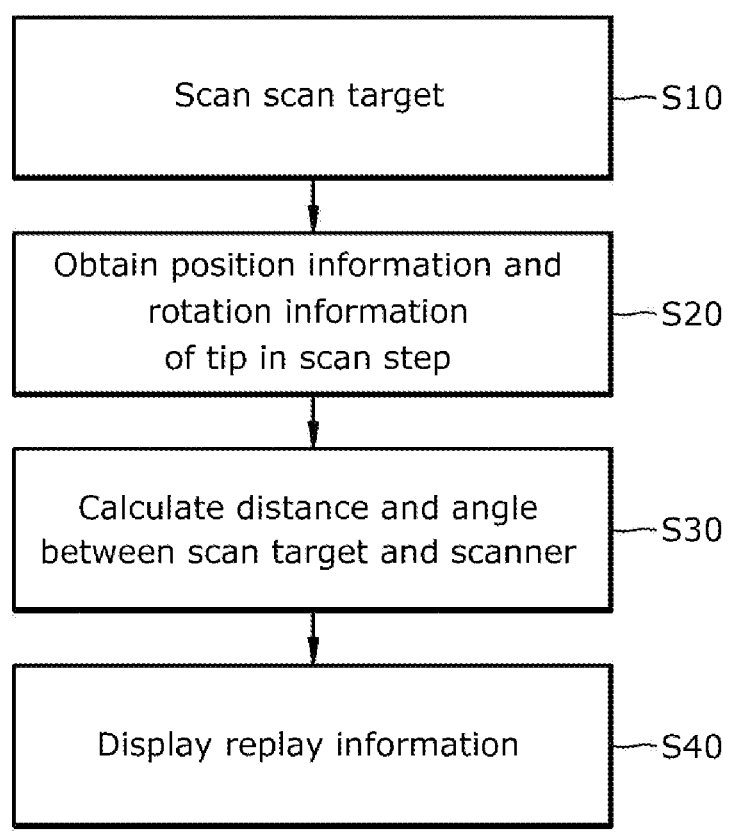
FIG. 1 is a schematic flowchart of a method of replaying a scanning process according to the present disclosure.

S10: scanning step
S11: 2-D image acquisition step
S12: 3-D image generation step
S13: alignment step
S20: information acquisition step
S30: calculation step
S40: display step
T1, T2, T3, T4, T5, T6: scan point
1: scan target
M: model
10: scan display unit
12: shade
14: pattern
20: scan execution unit
21: scanner tip
30: manipulation interface unit
31: replay manipulation unit
32 scan time indication unit
32a: slider bar
32b: search button
33: replay speed control unit
33a: replay speed deceleration unit
33b: replay speed acceleration unit
34: scanner tip display/release button
35: scan area display/release button
36: replay/stop button
40: scan portion selection unit
41: upper jaw selection unit
42: lower jaw selection unit
43: occlusion selection unit
100: scanner
110: moving path

BEST MODE

Hereinafter, some embodiments of the present disclosure will be described in detail with reference to exemplary drawings. In adding reference numerals to the elements of each drawing, it should be noted that the same elements have the same reference numerals as much as possible even if they are displayed in different drawings. Furthermore, in describing embodiments of the present disclosure, when it is determined that a detailed description of the related well-known configuration or function hinders understanding of an embodiment of the present disclosure, the detailed description thereof will be omitted.

Furthermore, in describing elements of an embodiment of the present disclosure, terms, such as a first, a second, A, B, (a), and (b), may be used. Such terms are used only to distinguish one component from the other component, and the essence, order, or sequence of a corresponding component is not limited by the terms. All terms used herein, including technical or scientific terms, have the same meanings as those commonly understood by a person having ordinary knowledge in the art to which an embodiment pertains, unless defined otherwise in the specification. Terms, such as those commonly used and defined in dictionaries, should be construed as having the same meanings as those in the context of a related technology, and are not construed as being ideal or excessively formal unless explicitly defined otherwise in the specification.

Figure 2:
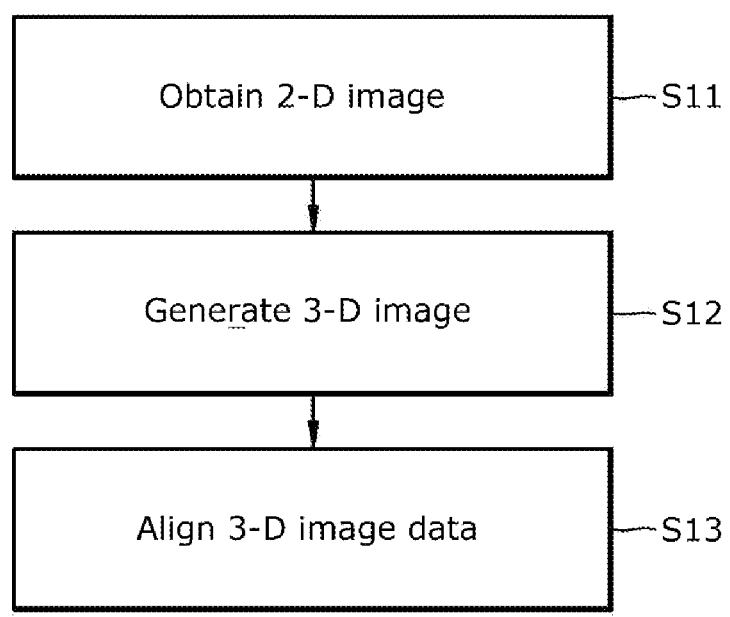
FIG. 2 is a flowchart more specifically illustrating a scanning step in the method of replaying a scanning process according to the present disclosure.

FIG. 1 is a schematic flowchart of a method of replaying a scanning process according to the present disclosure. FIG. 2 is a flowchart more specifically illustrating a scanning step in the method of replaying a scanning process according to the present disclosure.

Referring to FIGS. 1 and 2, the method of replaying a scanning process according to the present disclosure includes a scanning step S10 of obtaining scan data by scanning a scan target 1 by using a scanner. In the scanning step S10, light reflected by a surface of the scan target 1 is introduced into the scanner through an opening part formed at one end of the scanner. The light introduced into the scanner is received through a camera disposed within the scanner. The camera obtains the received light as digital scan data through an imaging sensor connected to the camera. In this case, the scan data may be at least one two-dimensional (2-D) image data (this step may correspond to step S11 of obtaining 2-D image data in the scanning step S10). Meanwhile, the obtained 2-D image data may be displayed in a scan execution unit 20 in real time or may be used as data for generating three-dimensional (3-D) volume data when the obtained 2-D image data is generated as the 3-D volume data by structural light radiated from an optical projector, additionally disposed within the scanner, toward the scan target 1.

Meanwhile, after the 2-D image data is obtained through the camera and the imaging sensor connected to the camera, the obtained 2-D image data may be formed to be converted into 3-D volume data by combining the 2-D image data (a 3-D image sensing step S12). The 3-D volume data may be formed to include a voxel having graphic information in a 3-D space. As a result, the scan data may be displayed in a user interface by a set of such 3-D volume data. However, in order for the scan data to be displayed in the user interface, an alignment step S13 of aligning a plurality of the 3-D volume data needs to be performed so that the plurality of 3-D volume data is connected and aligned without fragmentarily displaying each of the 3-D volume data. A connection between the 3-D volume data generated through the alignment step S13, the alignment of coordinates, etc. are performed. Such an alignment process may be performed in various ways, but the alignment step S13 may be performed using an iterative closest point (ICP) algorithm for connecting an overlap portion of the other data with one data, preferably.

Furthermore, as described above, while the scanning step S10 is performed, state information of the scanner may be obtained along with the scan data (an information acquisition step S20). In this case, the state information of the scanner may be variously obtained, but position information and rotation information of the camera disposed within the scanner may be obtained. The number of cameras disposed within the scanner may be one or more. The number of cameras whose position information and rotation information are obtained may also be one or more. To obtain the position information and the rotation information through the camera is for finally obtaining distance information between the scanner and the scan target.

Figure 3:
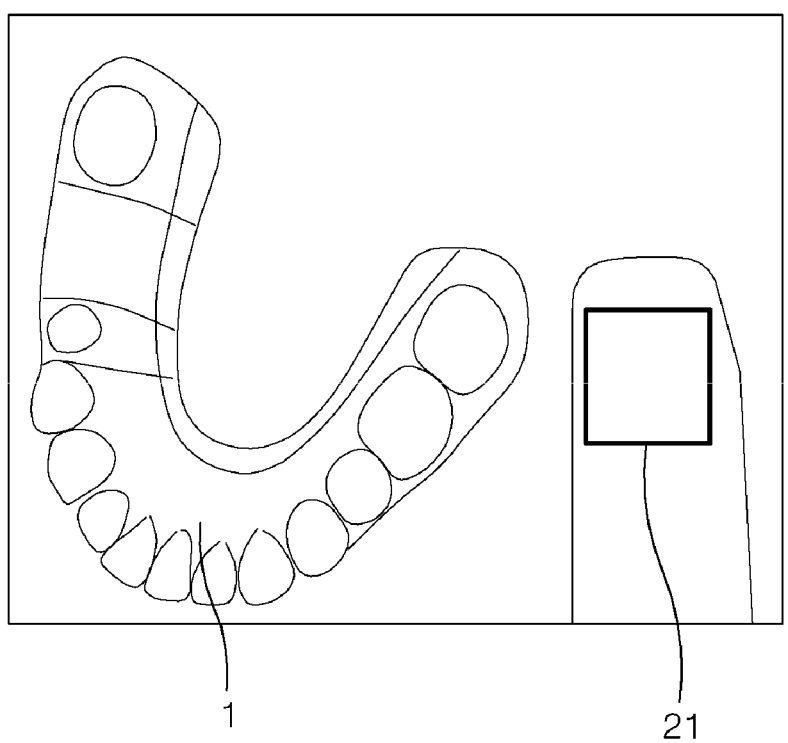
FIG. 3 is a schematic diagram of a scan target and a scanner for scanning the scan target in the method of replaying a scanning process according to the present disclosure.

FIG. 3 is a schematic diagram of the scan target and the scanner for scanning the scan target in the method of replaying a scanning process according to the present disclosure.

Referring to FIG. 3, the scan target 1 is scanned through the scanner. The scan target 1 may be a plaster cast obtained through impression taking or may be an actual mouth including teeth and gums of a patient. The scanner includes various types of scanners. However, preferred to adopt and use a handheld type 3-D scanner when comprehensively considering characteristics, use convenience, etc. of the present disclosure. Light reflected by the scan target 1 enters the scanner through a scanner tip of the scanner. The light may be formed as 3-D-modeled scan data after 2-D and 3-D image acquisition and alignment are performed on the light.

Figure 4:
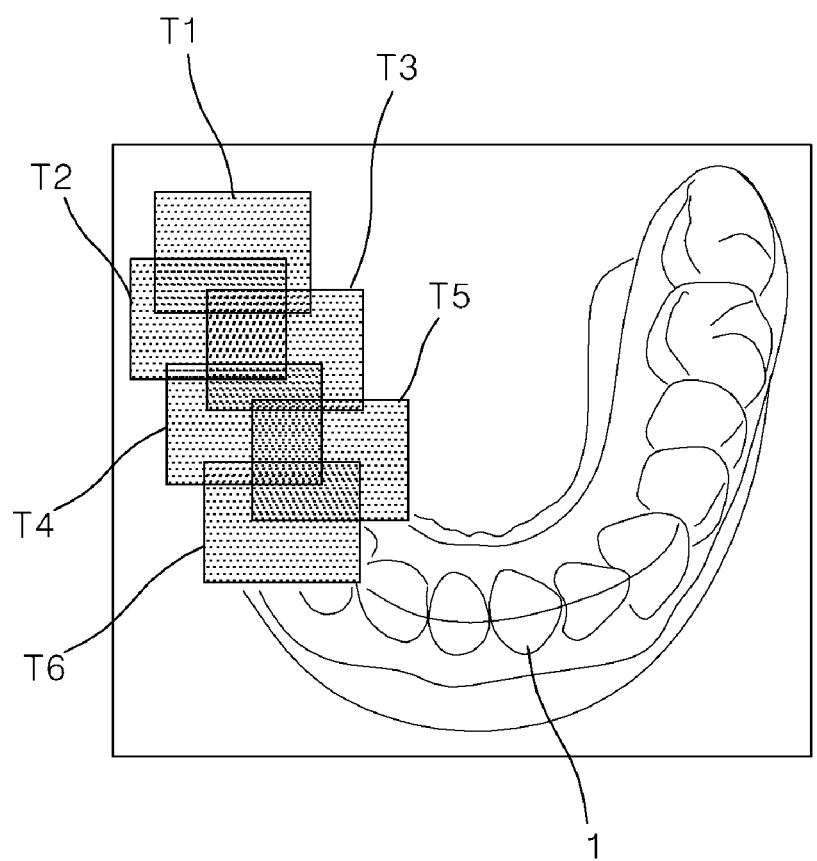
FIG. 4 is a diagram schematically describing a process of performing scanning while performing the scanning from T1 to T6 when the scanner scans the scan target in the method of replaying a scanning process according to the present disclosure.
Figure 5:
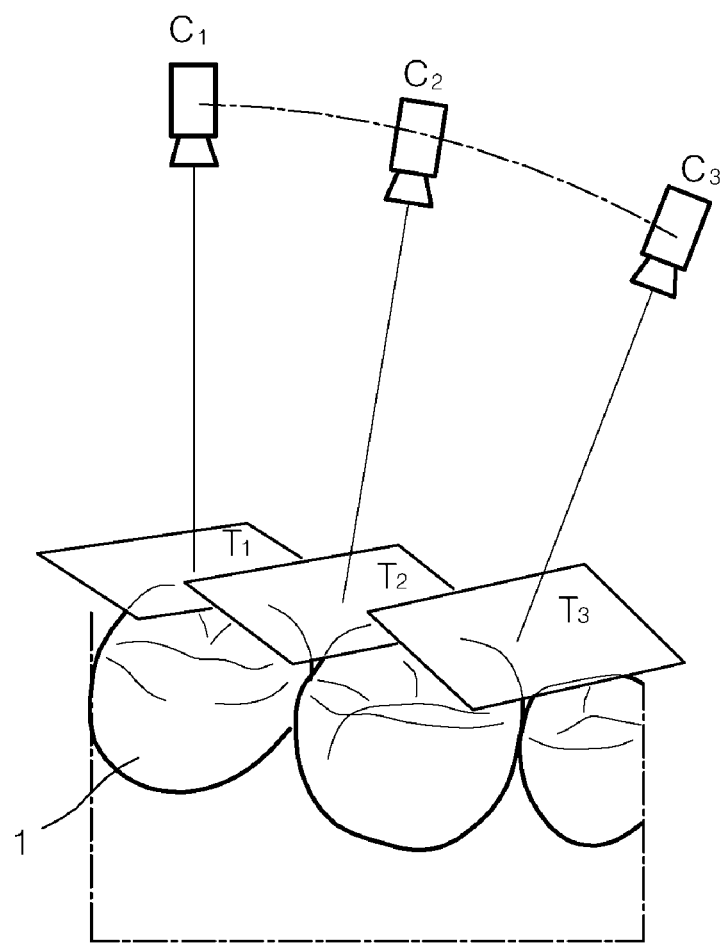
FIG. 5 is a diagram schematically illustrating a relation between a camera embedded in the scanner and the scan target when the scan target is scanned.

FIG. 4 is a diagram schematically describing a process of performing scanning while performing the scanning from T1 to T6 when the scanner scans the scan target in the method of replaying a scanning process according to the present disclosure. FIG. 5 diagram schematically illustrating a relation between the camera embedded in the scanner and the scan target when the scan target is scanned.

Referring to FIGS. 4 and 5, the scanner may perform scanning on the scan target 1 while moving from one end of the scan target 1 to the other end thereof. Meanwhile, when a user performs scanning through the scanner, the scanning is sequentially performed from a first scan point T1 to next scan points T2, T3, T4, T5, and T6. In the process of performing the scanning, the scan points T1, T2, T3, T4, T5, and T6 may have portions that overlap neighboring scan points. As the scanning is performed so that the overlap portions are present, data is aligned, and one model data for the scan target may be finally generated.

Meanwhile, when the scanner performs the scanning, position information of the camera obtained in the information acquisition step S20 may have a form of a 3-D orthogonal Cartesian coordinate system represented as x, y, and z values. The position information of the camera may be indicated as a relative position based on a specific point. Preferably, coordinates when scanning is started may be set as a starting point (0, 0, 0), and relative coordinates of each scan points may be obtained.

Rotation information of the camera may be obtained in the form of three angles represented as ($\alpha$, $\beta$, $\gamma$). In this case, $\alpha$ may mean an angle of the camera in an xy plane, $\beta$ may mean an angle of the camera in a yz plane, and $\gamma$ may mean an angle of the camera in a zx plane. Furthermore, the rotation information of the camera may be obtained in the form of a 3×3 matrix. In this case, the 3×3 matrix may include information on an angle in the xy plane, an angle in the yz plane, and an angle in the zx plane. The rotation information means information on a tilt angle with respect to a reference position not information on a rotation speed, etc. The rotation information of the camera may be converted from the form of the three angles, represented as ($\alpha$, $\beta$, $\gamma$), to the form of the 3×3 matrix, if necessary, or may be converted from the form of the 3×3 matrix to the form of the three angles as a reverse case thereof.

Furthermore, as described above, the position information of the camera and the rotation information of the camera may be separately obtained in the forms of the 3-D orthogonal Cartesian coordinate system and the 3×3 matrix, respectively. The position information and rotation information of the camera may be obtained in the form of the 3×4 matrix at a time.

When the position information and rotation information of the camera are obtained, position information and rotation information of the scanner tip may be obtained from the obtained position information and rotation information of the camera by using position information and rotation information between the camera and the scanner tip. More specifically, the scanner tip is configured to have a given distance and given angle with respect to the camera in terms of a structural characteristic of the scanner based on position information and rotation information of the camera. Accordingly, if a distance between the camera and the scanner tip is added and an angle formed by the camera and the scanner tip is incorporated with respect to the position information and rotation information of the camera, the position information of the scanner tip and the rotation information of the scanner tip may be derived. In this case, the position information of the scanner tip may be variously indicated, but may use, as a reference, a portion corresponding to the center of a cross-sectional shape of the opening part of the scanner. Furthermore, the rotation information of the scanner tip may be an angle of a normal vector in a virtual plane including the cross section of the opening part of the scanner.

When the information acquisition step S20 is performed, a calculation step S30 of calculating relative information between the scanner and the scan target 1 based on the state information of the scanner may be performed. In the calculation step S30, the distance between the scanner tip and the scan target 1, which is obtained in the information acquisition step S20, may be measured. The distance may be obtained as distance data by calculating a straight-line distance and an angle between scan points (e.g., the scan points may correspond to T1, T2, T3, T4, T5, and T6, but are not limited to the six scan points, and may correspond to a plurality of points scanned when the scanning step S10 performed) and the scanner tip. Referring to FIG. 5, while the camera moves (from C1 to C2 and from C2 to C3), position information and rotation information of the camera may be obtained. Position information and rotation information of the scanner tip may be obtained based on the position information and rotation information of the camera.

Furthermore, distance and angle information between the scan target 1 and the scanner tip may be calculated. A moving path 110 of the scanner tip to be described later is generated based on the distance and angle information calculated in the calculation step S30.

Meanwhile, when the scanning step S10 is performed through the scanner, the position information and rotation information of the scanner tip may be changed depending on scan time. Accordingly, the position information and rotation information of the scanner tip may be formed to operate in conjunction with each other from the nature of data in a way to have information on a scan time when the position information and the rotation information are generated. Accordingly, the position information and rotation information of the scanner tip may be sequentially aligned in a scan time sequence. There is an advantage in that data can be aligned and replayed in a time sequence because position information and rotation information of the scanner tip are sequentially aligned in a scan time sequence.

FIGS. 6 to 14 are diagrams illustrating a process of generating scan model data in a user interface in a time sequence in the method of replaying a scanning process according to the present disclosure.

Generally referring to FIGS. 6 to 14, the method of replaying a scanning process according to the present disclosure may include a display step S40 of displaying the scan data in the user interface in the form of a 3-D model M by scanning the scan target 1. In the display step S40, the model M completed through a scanning process may be displayed, but a process of forming the model until the model is completed may be displayed.

Figure 6:
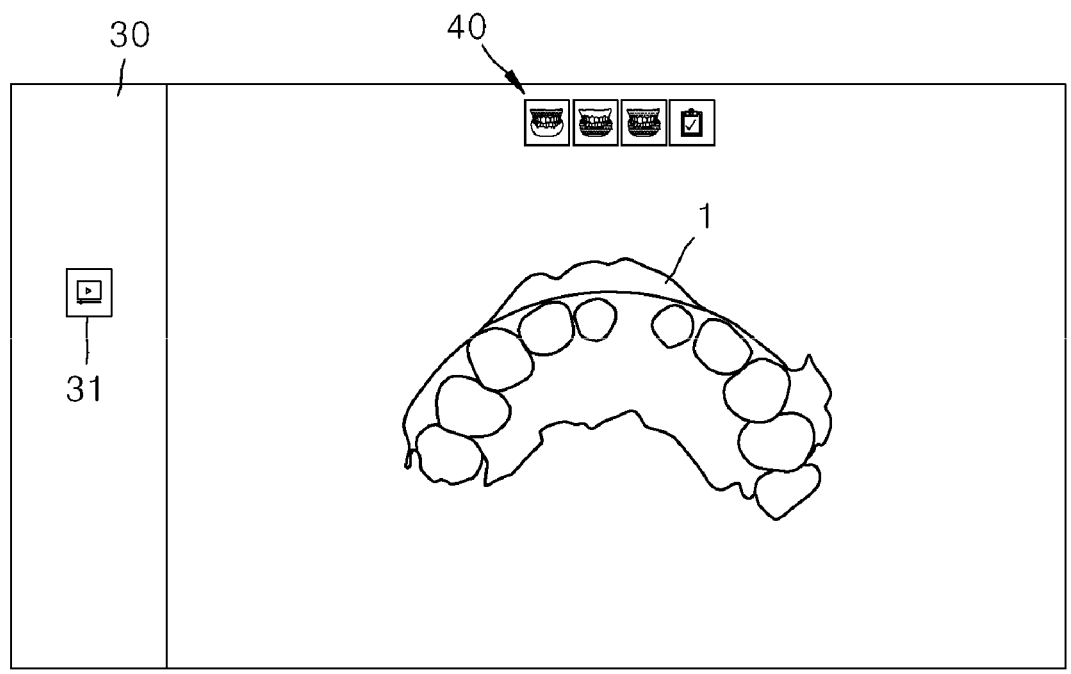
FIGS. 6 to 14 are diagrams illustrating a process of generating scan model data in a user interface in a time sequence in the method of replaying a scanning process according to the present disclosure.
Figure 7:
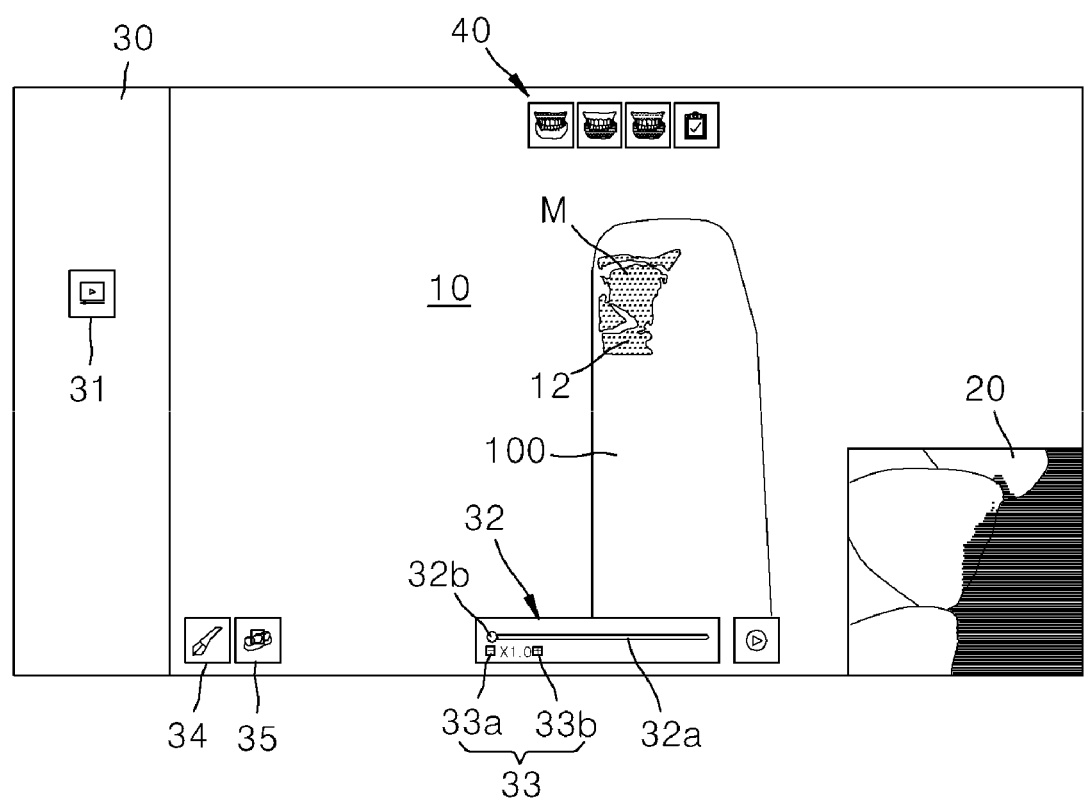
Figure 8:
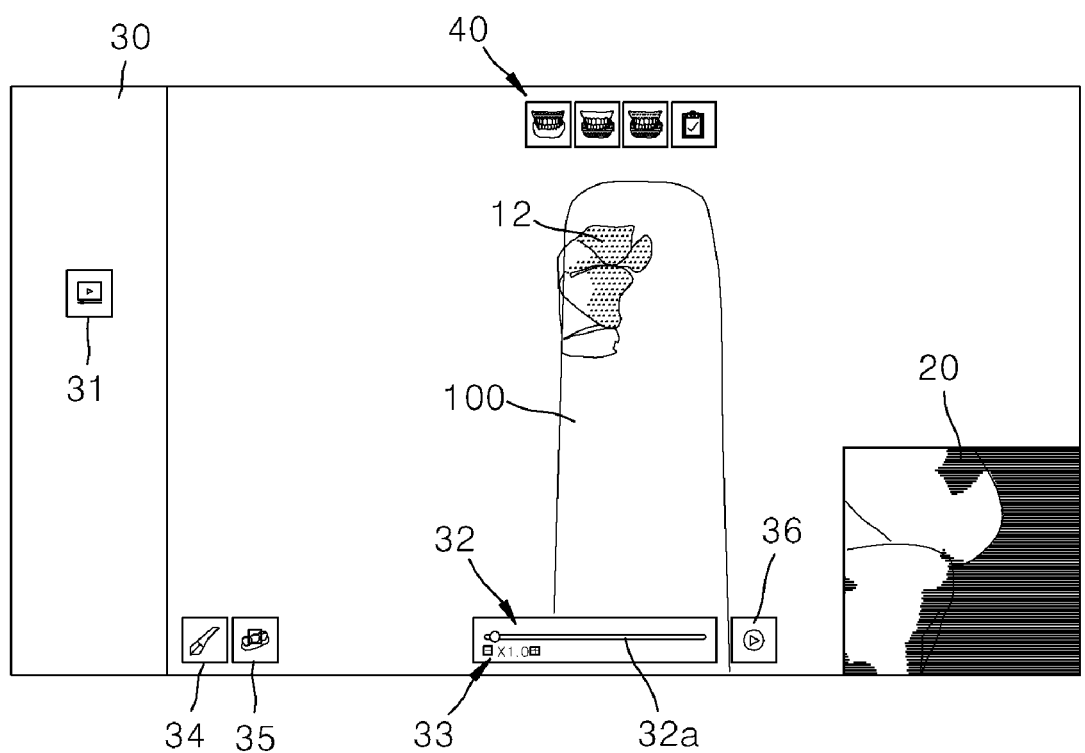
Figure 9:
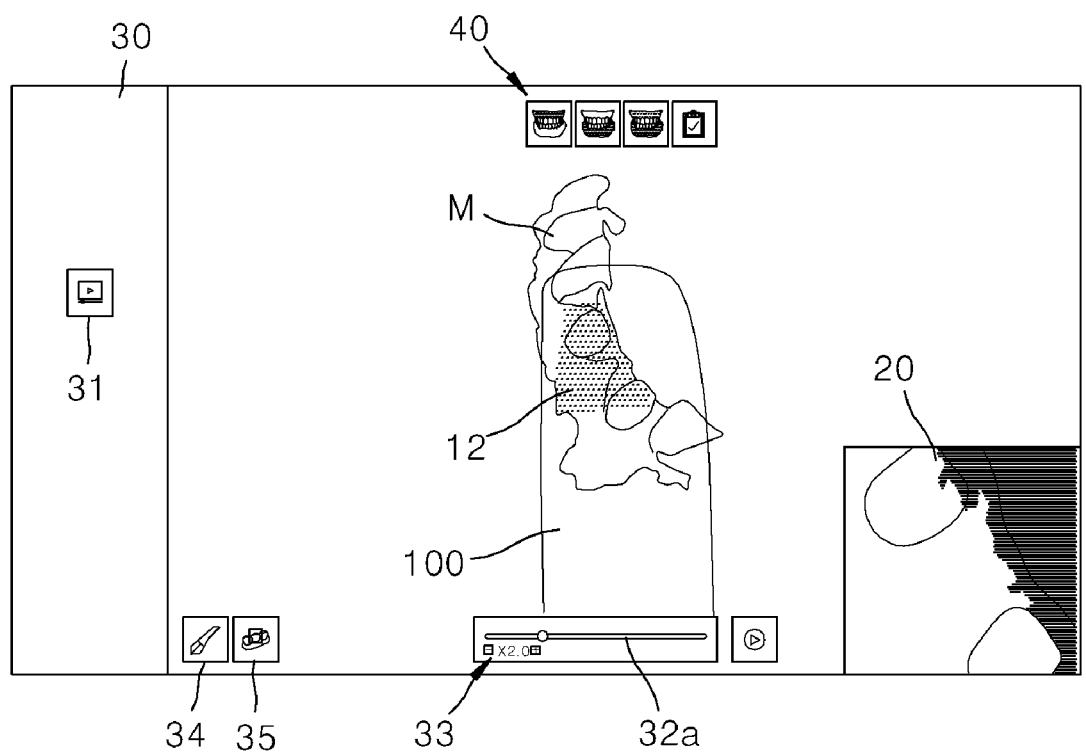
Figure 10:
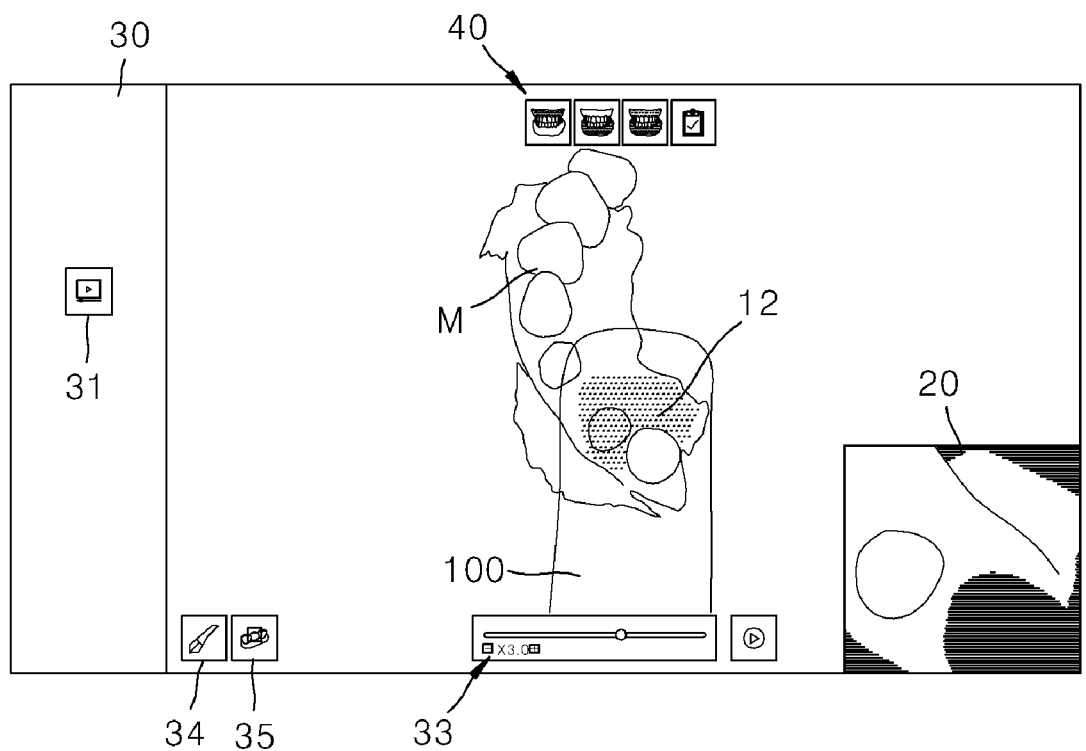
Figure 11:
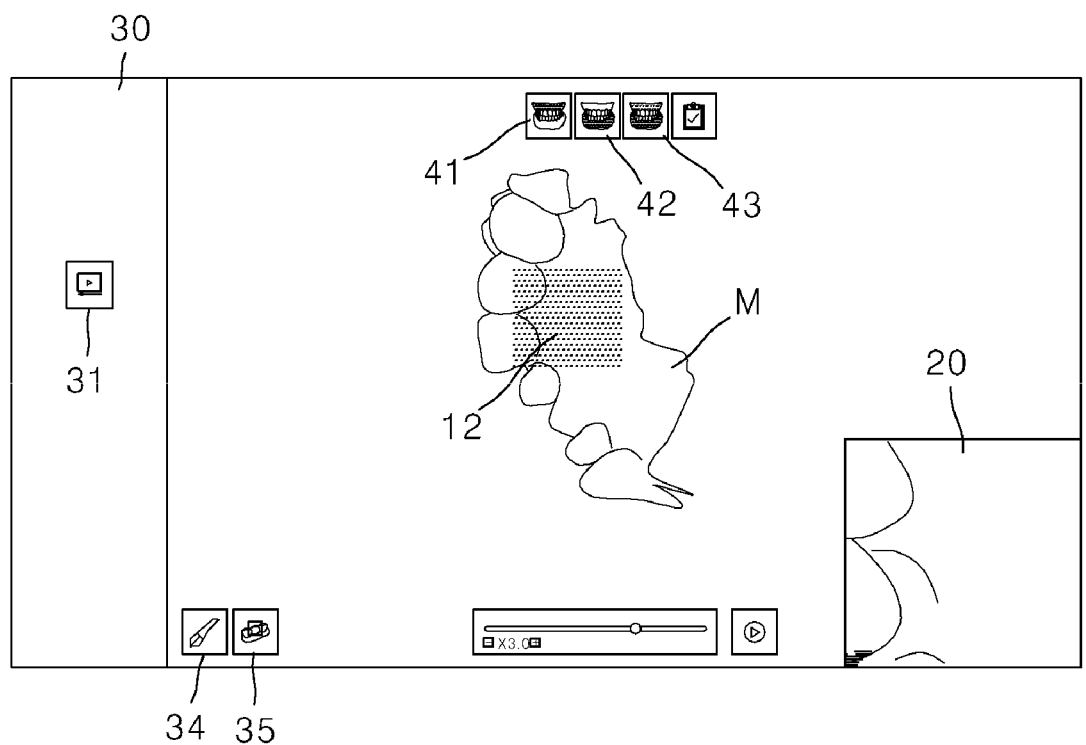
Figure 12:
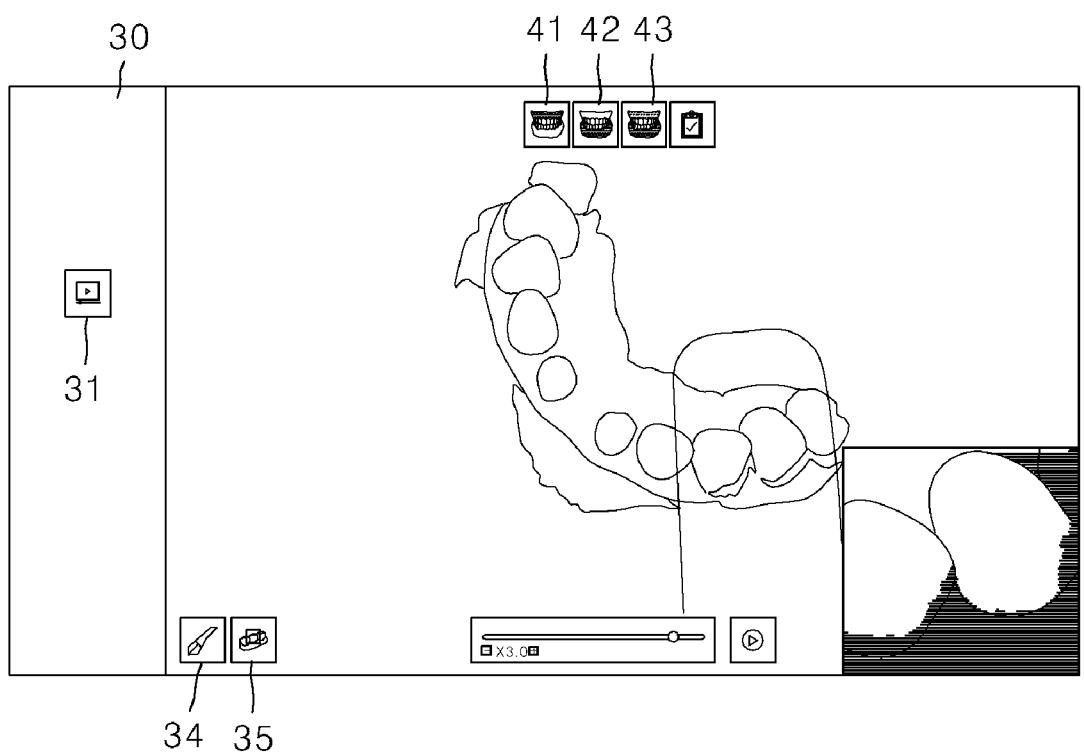

Referring to FIGS. 6 and 7, the user interface may include a scan display unit 10 on which scan data is displayed in the form of the 3-D model M, a scan execution unit 20 in which a scanning process is displayed, and a manipulation interface unit 30 in which a manipulation performed on the 3-D model. The scan execution unit 20 may perform scanning in real time or may visually display 2-D image data generated through the camera and the imaging sensor in a corresponding time when a scanning process is replayed. Meanwhile, the scan execution unit 20 and the scan display unit 10 may be formed to be displayed on the same screen, and may simultaneously replay a process of forming the 3-D model M in accordance with the same scan timing and 2-D image data obtained in a scanning process. Furthermore, the scan execution unit 20 may be isolated from the scan display unit 10. In order for the 3-D model M to be more importantly recognized, the scan execution unit 20 may be formed to occupy a smaller area than the scan display unit 10.

Meanwhile, the manipulation interface unit 30 may perform various manipulations on the 3-D model M. According to circumstances, if the results of scanning are different from those expected by a user, an option capable of deleting data of a specific portion, an option capable of checking data reliability of data of the 3-D model M, an option capable of checking an operating state (waiting, scanning, etc.) of the scanner, etc. may be included in the manipulation interface unit 30. In the present disclosure, however, the replay of a scanning process is primary, and an option button not related to the replay of a scanning process is omitted.

The manipulation interface unit 30 may include a replay manipulation unit 31. In general, the scan display unit 10 displays only the final data displayed by forming, in the form of the 3-D model M, data until scanning is terminated after the scanning is started, but a mode of the user interface may be changed into a replay mode by manipulating (e.g., clicking on) the replay manipulation unit 31.

When the mode of the user interface is changed into the replay mode, portions 32 to 36 corresponding to the replay mode may be additionally displayed on the lower side of the scan display unit 10. In the replay mode, a scan time indication unit 32 may temporally indicate the time when scanning was performed. In this case, the scan time may appear in a slider bar 32*a* in response to an operation of a search button 32*b* moving from one end to the other end. That is, when the search button 32*b* is positioned at one end (e.g., the end on the left of the slider bar), the scan time may correspond to a scan start time. When the search button 32*b* is positioned at the other end (e.g., the end on the right of the slider bar), the scan time may correspond to a scan end time. In the display step 340 according to the present disclosure, a process of forming scan data may be replayed in the replay mode in a way to be sequentially displayed over time. The process of forming scan data means that the scan data obtained in the scanning step 310 is displayed in a time sequence in which the scan data is obtained.

Meanwhile, the scan time indication unit 32 may move to scan timing corresponding to a corresponding point by clicking on a specific point in the slider bar 32*a*. A scanning process may be replayed from the scan timing corresponding to the corresponding point. Alternatively, the scan time indication unit 32 may move to scan timing desired by a user by clicking on and dragging & dropping the search button 32*b*.

Furthermore, the display step S40 may be configured to adjust a replay speed through a replay speed control unit 33 formed in the user interface in replaying a process of forming scan data. The replay speed control unit 33 includes a replay speed deceleration unit 33*a* and a replay speed acceleration unit 33*b*. The replay speed deceleration unit 33*a* may be commonly indicated as a mark of "−". The replay speed acceleration unit 33*b* may be commonly indicated as a mark of "+". A replay speed now applied when a replay process is performed may be displayed between the replay speed deceleration unit 33*a* and the replay speed acceleration unit 33*b*. The replay speed may be variously adjusted like ×0.5, ×1.0, ×1.5, ×2.0, ×2.5, ×3.0, etc. of a reference speed.

Meanwhile, referring to FIGS. 7 to 12, in the display step S40, in replaying a process of forming scan data, one end of a shape 100 of the scanner including the scanner tip may be displayed in the user interface (more specifically, the scan display unit 10). As the shape 100 of the scanner is displayed on the scan display unit 10, how scanning was performed where and through how much rotation (tilt angle) when a user scans the scan target 1 may be visually checked. A portion for which the scanning was insufficient may be red back. Furthermore, the shape 100 of the scanner may be semi-transparently displayed in the user interface, so that a state of the scanner including the scanner tip and scan data may be simultaneously replayed. That is, when the shape 100 of the scanner is opaquely displayed, some of or the entire scan data in which scanner graphics are displayed in the form of the 3-D model M may be covered. In this case, the scan data and a state of the scanner including the scanner tip may be checked by adjusting transparency of the shape 100 of the scanner.

In this case, the 3-D model M and the shape 100 of the scanner including the scanner tip may be replayed so that the position information and rotation information of the scanner tip and the distance and angle information between the scanner tip and the scan target 1, obtained in the information acquisition step S20 and the calculation step S30, are displayed. That is, when a scanning process is replayed in the display step S40, piece of information sequentially obtained over time may be visually displayed on the scan display unit 10. In particular, in scanning the scan target 1, if the scanner has rotated, the 3-D model M may be represented to rotate as the scanner rotates with respect to the scan target 1 when the scanner scans the scan target 1.

Meanwhile, if only a process of forming scan data is to be checked by covering the scanner tip when a scanning process is replayed, the shape 100 of the scanner including the scanner tip may not be displayed by clicking on a scanner tip display/release button 34 formed on one side of the scan display unit 10. As the shape 100 of the scanner is not displayed, a process of obtaining scan data that form the 3-D model M can be more closely monitored.

Figure 13:
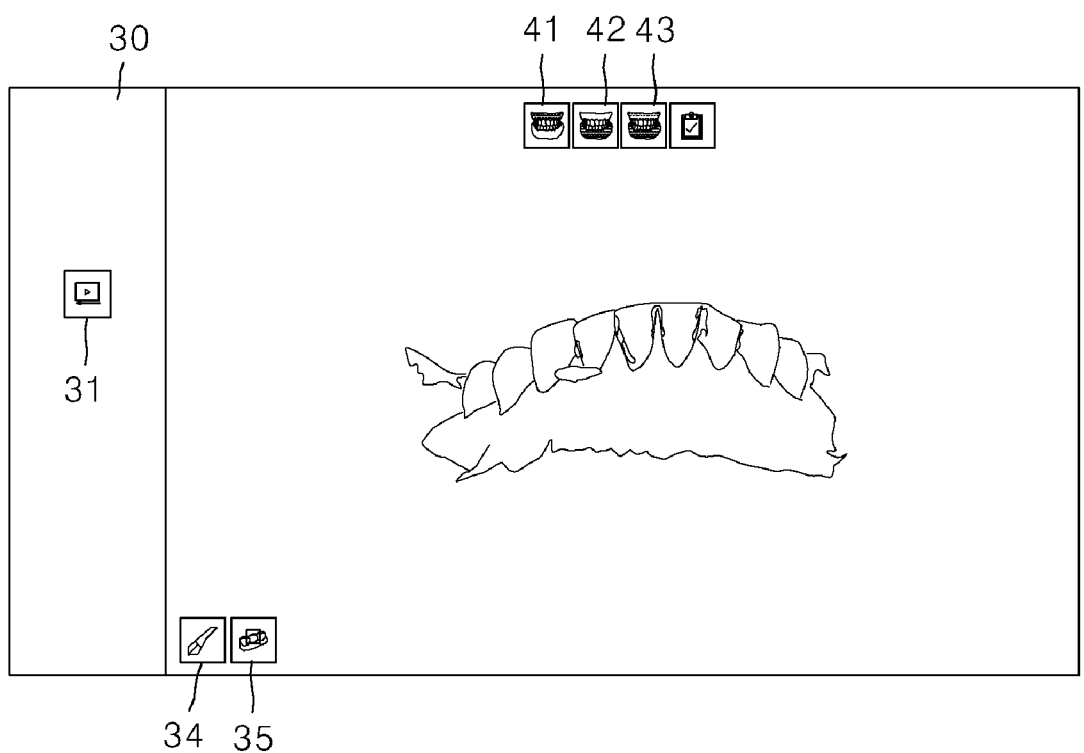
Figure 14:
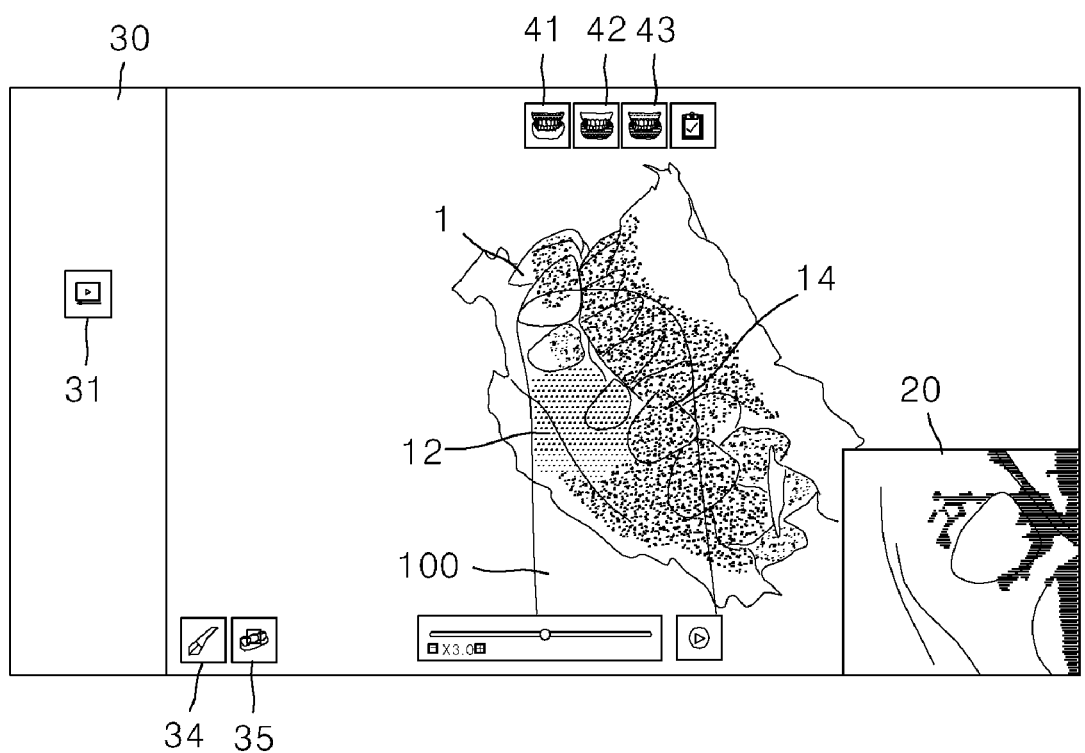

Referring to FIGS. 13 and 14, a scan portion selection unit 40 may be formed at one end of the scan display unit 10. For example, the scan portion selection unit 40 may be formed on the upper side of the scan display unit 10. The scan portion selection unit 40 may include an upper jaw selection unit 41, a lower jaw selection unit 42, and an occlusion selection unit 43. If the replay mode is entered by enabling (e.g., clicking on) the replay manipulation unit 31, only a process of scanning the upper jaw may be replayed when the upper jaw selection unit 41 is selected, and only a process of scanning the lower jaw may be replayed when the lower jaw selection unit 42 is selected. Furthermore, when the occlusion selection unit 43 is selected in the replay mode, only a process of scanning an occlusion form of the upper and lower laws in order to form the occlusion of the upper jaw and the lower jaw may be replayed. In this case, a portion whose occlusion information is obtained may be displayed so that the upper jaw and the lower jaw are distinguished from each other. The portion may be displayed using at least one visual method of color, a shade, and a pattern 14. Meanwhile, the process of scanning the upper jaw, the process of scanning the lower jaw, and the process of scanning the occlusion may be divided in a time sequence. In order to separate and replay the scanning processes according to each scanning process, scan data and position information and rotation information of the scanner tip may be divided into a plurality of groups in a time sequence. There is an advantage in that a user can rapidly take only feedback for a specific scanning process although the user does not check the entire scanning process because a process of scanning the upper jaw, a process of scanning the lower jaw, and a process of scanning occlusion can be separated and viewed as described above.

Meanwhile, in the replay mode, a portion scanned at each piece of scan timing may be displayed in the 3-D model M, displayed on the scan display unit 10, in the form of a shade 12. A user may receive feedback for a portion for which scanning was insufficient with reference to a moving path of the shade 12, etc., and may use the feedback as reference data in subsequent scanning.

Figure 15:
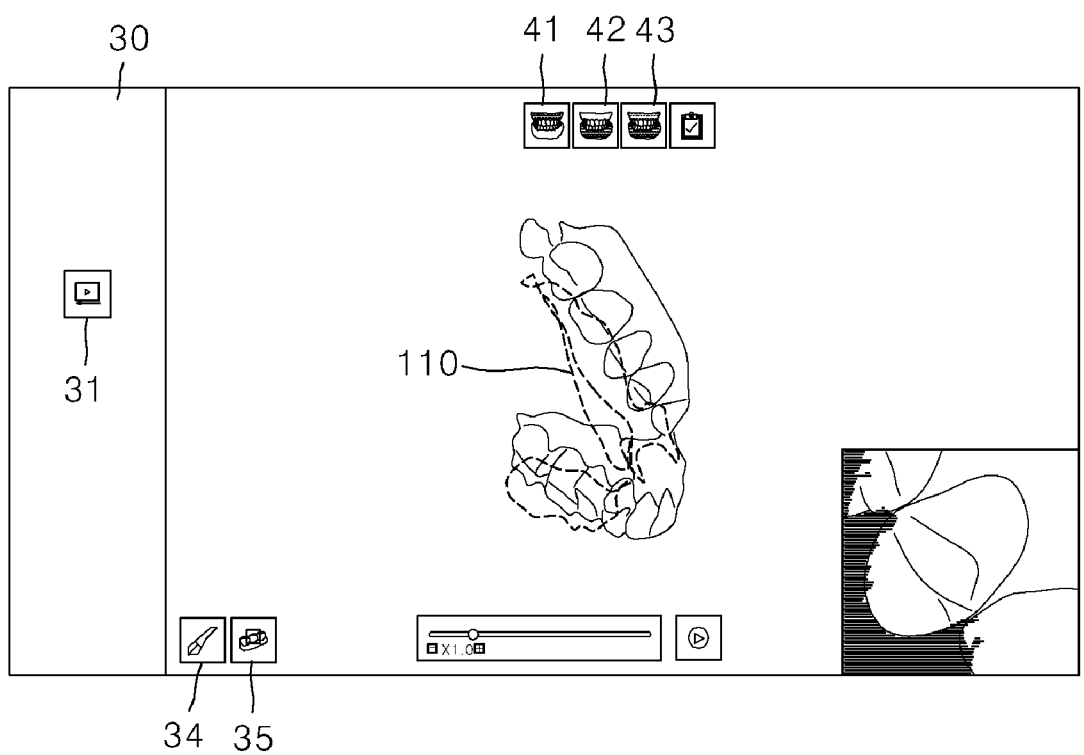
FIG. 15 is a diagram illustrating that a scan path is displayed in the user interface in the method of replaying a scanning process according to the present disclosure.

FIG. 15 is a diagram illustrating that a scan path is displayed in the user interface in the method of replaying a scanning process according to the present disclosure.

Referring to FIG. 15, in the method of replaying a scanning process according to the present disclosure, the display step S40 may additionally display a moving path 110 of the scanner tip. The moving path 110 of the scanner tip is obtained by connecting pieces of position information of the scanner tip in a time sequence. Accordingly, each of points constituting the moving path 110 of the scanner tip may include scan time information (scan timing). When a part in the moving path 110 of the scanner tip is selected, the scanner tip may move to scan timing (replay position) corresponding to the corresponding point, so that replay may be performed at the scan timing. Accordingly, there are advantages in that a user can visually check the moving path 110 of the scanner tip and can rapidly receive feedback for a scanning process by taking the feedback based on the moving path 110 of the scanner tip.

The above description is merely a description of the technical spirit of the present disclosure, and those skilled in the art may change and modify the present disclosure in various ways without departing from the essential characteristic of the present disclosure.

Accordingly, the embodiments described in the present disclosure should not be construed as limiting the technical spirit of the present disclosure, but should be construed as describing the technical spirit of the present disclosure. The technical spirit of the present disclosure is not restricted by the embodiments. The range of protection of the present disclosure should be construed based on the following claims, and all of technical spirits within an equivalent range of the present disclosure should be construed as being included in the scope of rights of the present disclosure.

INDUSTRIAL APPLICABILITY

The present disclosure provides the method of replaying a scanning process, which can simulate and display a scanning process of obtaining previously stored scan data from the scan data.

The invention claimed is:

1. A method of replaying a scanning process, comprising:
a scanning step of obtaining scan data by scanning a scan target by using a scanner;
an information acquisition step of obtaining state information of the scanner obtained in the scanning step;
a calculation step of calculating relative information between the scanner and the scan target based on the state information of the scanner obtained in the information acquisition step; and
a display step of displaying, in a user interface, the scan data obtained by scanning the scan target to replay a process of forming the scan data,
wherein the scan data is displayed in a form of a three-dimensional (3-D) model in the display step,
wherein the 3-D model is represented to rotate in the user interface by relative information between the scanner and the scan target as the scanner rotates with respect to the scan target,
wherein, when replaying the process of forming the scan data, the mode of the user interface is changed into the replay mode, and
wherein the scan data obtained in the scanning step is displayed in a time sequence in which the scan data is obtained in the replay mode so that a process of forming the 3-D model until the 3-D model is completed is displayed.

2. The method of claim 1, wherein the scanning step comprises:
a two-dimensional (2-D) image acquisition step of obtaining at least one 2-D image data by receiving light incident through an opening part formed at one end of the scanner;
a 3-D image generation step of converting, into 3-D volume data, the at least one 2-D image data obtained in the 2-D image acquisition step; and
an alignment step of aligning a plurality of the 3-D volume data so that the 3-D volume data is connected and aligned.

3. The method of claim 1, wherein the information obtained in the information acquisition step comprises position information and rotation information of a camera.

4. The method of claim 3, wherein the position information of the camera is obtained in a form of a 3-D orthogonal Cartesian coordinate system represented as x, y, and z values.

5. The method of claim 3, wherein the rotation information of the camera is obtained in a form of a 3×3 rotation matrix.

6. The method of claim 3, wherein the position information of the camera and the rotation information of the camera are obtained together in a form of a 3×4 matrix.

7. The method of claim 3, wherein in the information acquisition step, position information and rotation information of a scanner tip are obtained based on the position information of the camera and the rotation information of the camera.

8. The method of claim 7, wherein the position information and rotation information of the scanner tip are formed to operate in conjunction with a scan time.

9. The method of claim 1, wherein in the display step, a process of forming the scan data is replayed in a way to be sequentially displayed over time.

10. The method of claim 9, wherein in the display step, in replaying the process of forming the scan data, a replay speed is adjustable through a replay speed control unit formed in the user interface.

11. The method of claim 9, wherein in the display step, in replaying the process of forming the scan data, a replay position is adjustable through a scan time indication unit formed in the user interface.

12. The method of claim 9, wherein in the display step, in replaying the process of forming the scan data, one end of a shape of the scanner comprising a scanner tip is displayed in the user interface.

13. The method of claim 12, wherein the shape of the scanner is semi-transparently displayed in the user interface, and the state and scan data of the scanner comprising the scanner tip are simultaneously replayed.

14. The method of claim 13, wherein in the display step, a moving path of the scanner tip is additionally displayed.

15. The method of claim 14, wherein:
the moving path of the scanner tip comprises scan time information, and
when a part in the moving path of the scanner tip is selected, the scanner tip moves to a replay position corresponding to the part.

16. The method of claim 8, wherein the scan data and the position information and rotation information of the scanner tip are divided into a plurality of groups in a time sequence.

17. A replaying device, comprising:
a memory; and
a processor operably coupled to the memory, wherein the processor, in executing program instructions stored in the memory is configured, to perform:
a scanning step of obtaining scan data by scanning a scan target by using a scanner;
an information acquisition step of obtaining state information of the scanner obtained in the scanning step;
a calculation step of calculating relative information between the scanner and the scan target based on the state information of the scanner obtained in the information acquisition step; and
a display step of displaying, in a user interface, the scan data obtained by scanning the scan target to replay a process of forming the scan data,
wherein the scan data is displayed in a form of a three-dimensional (3-D) model in the display step,
wherein the 3-D model is represented to rotate in the user interface by relative information between the scanner and the scan target as the scanner rotates with respect to the scan target,
wherein, when replaying the process of forming the scan data, the mode of the user interface is changed into the replay mode, and
wherein the scan data obtained in the scanning step is displayed in a time sequence in which the scan data is obtained in the replay mode so that a process of forming the 3-D model until the 3-D model is completed is displayed.

18. The device of claim 17, wherein the processor is further configured to perform, in performing the scanning step:
a two-dimensional (2-D) image acquisition step of obtaining at least one 2-D image data by receiving light incident through an opening part formed at one end of the scanner;
a 3-D image generation step of converting, into 3-D volume data, the at least one 2-D image data obtained in the 2-D image acquisition step; and
an alignment step of aligning a plurality of the 3-D volume data so that the 3-D volume data is connected and aligned.

19. The device of claim 17, wherein the information obtained in the information acquisition step comprises position information and rotation information of a camera.

20. The device of claim 19, wherein the position information of the camera is obtained in a form of a 3-D orthogonal Cartesian coordinate system represented as x, y, and z values.

* * * * *